United States Patent [19]

Schneider

[11] Patent Number: 5,733,902
[45] Date of Patent: Mar. 31, 1998

[54] COMPOUNDS HAVING ANTIPROGESTATIONAL AND ANTI-ESTROGENIC ACTIVITIES FOR THE TREATMENT OF HORMONE-DEPENDENT TUMORS

[75] Inventor: Martin Schneider, Berlin, Germany

[73] Assignee: Schering Aktiengesellschaft, Berlin, Germany

[21] Appl. No.: 195,046

[22] Filed: Feb. 14, 1994

Related U.S. Application Data

[63] Continuation of Ser. No. 548,343, Jul. 5, 1990, abandoned, which is a continuation of Ser. No. 252,612, Oct. 3, 1988, abandoned.

[30] Foreign Application Priority Data

Oct. 1, 1987 [DE] Germany ............ 37 33 478.6

[51] Int. Cl.$^6$ .................. A61K 31/595; A61K 31/56
[52] U.S. Cl. .................. 514/177; 514/168; 514/191; 514/170; 514/182
[58] Field of Search .................. 514/168, 171, 514/170, 177, 182

[56] References Cited

U.S. PATENT DOCUMENTS

| | | | |
|---|---|---|---|
| 4,656,187 | 4/1987 | Black et al. | 514/422 |
| 4,670,426 | 6/1987 | Zor et al. | 514/171 |
| 4,732,904 | 3/1988 | Morgan | 514/357 |
| 4,760,053 | 7/1988 | Labrie | 514/15 |
| 4,775,660 | 10/1988 | Labrie | 514/15 |
| 4,775,661 | 10/1988 | Labrie | 514/15 |
| 4,857,519 | 8/1989 | Paris | 514/182 |

FOREIGN PATENT DOCUMENTS 01105 2/1986 WIPO.

OTHER PUBLICATIONS

Hissom et al., "Progestin Effects on Growth in the Human Breast Cancer Cell Line T-47D-... etc", Biochemical and Biophysical Research Communications, vol. 145, No. 2, 1987, Jun. 15, 1987 pp. 706-711.

Bardon, et al: Steroid Receptor-mediated Cyclotoxicity of an Antiestrogen and an Antprogestin in Breast Cancer Cells, Cancer Research, 47, 1441-1448 (1987).

CA : vol. 107 : 52276(s) (1987).

CA : vol. 107 : 17986(b) (1987).

*Primary Examiner*—Theodore J. Criares
*Attorney, Agent, or Firm*—Millen, White, Zelano, & Branigan, P.C.

[57] ABSTRACT

Agents, containing at least one compound having anti-progestational activity and at least one compound having anti-estrogenic activity, are suitable for the treatment of hormone-dependent tumors.

47 Claims, 1 Drawing Sheet

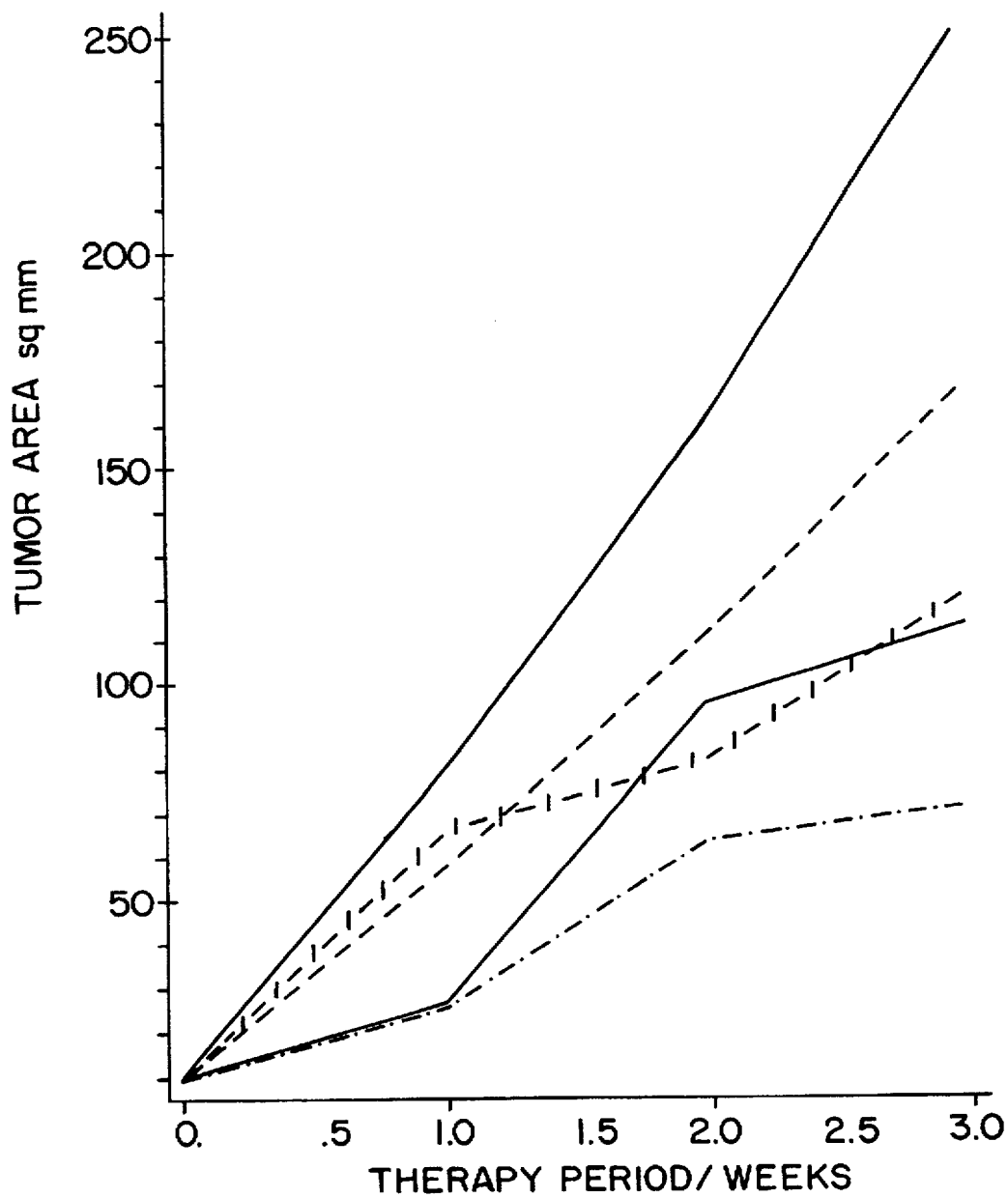

COMPOUNDS HAVING ANTIPROGESTATIONAL AND ANTI-ESTROGENIC ACTIVITIES FOR THE TREATMENT OF HORMONE-DEPENDENT TUMORS

This application is a continuation of application Ser. No. 07/548,343, filed Jul. 5, 1990 abandoned, which is a continuation of Ser. No. 08/252,612, filed Oct. 3, 1988, now abandoned.

BACKGROUND OF THE INVENTION

The invention relates to agents for the treatment of hormone-dependent tumors, containing at least one compound having antiprogestational activity (AG) and at least one compound having anti-estrogenic activity (AE), as to the use of such agents for the treatment of hormone-dependent tumors.

Compounds exhibiting anti-estrogenic activity are suitable for the treatment of diseases caused by estrogens or dependent on estrogens, for example for the treatment of estrogen-dependent tumors, such as mamma carcinoma, prostate hyperplasia, or meningioma.

Thus, for example, the anti-estrogen tamoxifen is employed for the palliative treatment of nonoperable mamma carcinoma as well as for adjuvant therapy after primary treatment of mamma carcinoma. However, the disease is not cured by tamoxifen. Gestagens or aromatase inhibitors are utilized for secondary therapy. Comparable response rates are obtained in premenopause by ovarieotomy, tamoxifen, or LHRH analogs (LHRH= luteinizing hormone releasing hormones) (Lit. H. T. Mouridsen and R. Paridaens, Eur. J. Cancer Clin. Oncol. 24: 99–105, 1988).

In more recent times, the use of antigestagens in the realm of tumor therapy, especially for the indication of mamma carcinoma, has likewise been under discussion. A report on a first phase II study with 17β-hydroxy-11β-(4-dimethylaminophenyl)-17α-(prop-1-ynyl)estra-4,9-dien-3-one on post menopausal and, respectively, ovariectomized female patients resistant to endocrine therapy, suffering from metastasizing mamma carcinoma, has been rendered by Maudelonde et al. in "Hormonal Manipulation of Cancer", Eds. J. G. M. Klijn, R. Paridaens and J. A. Folkens in Raven Press, p. 55 (1987).

SUMMARY OF THE INVENTION

This invention provides useful pharmaceutical compositions for the treatment of hormone-dependent tumors, e.g., to make medicinal agents for the treatment of hormone-dependent tumors exhibiting a high efficacy, and possibly a higher efficacy in comparison to the conventional agents.

Upon further study of the specification and appended claims, further objects and advantages of this invention will become apparent to those skilled in the art.

This invention provides a combination of AG and AE, whereby the efficacy of the individual components is considerably enhanced. The combination according to this invention is based on the realization that the growth of hormone-dependent tumors is dependent simultaneously on estrogens and gestagens. Thus, estrogen receptors as well as progesterone receptors could be identified in a large portion of mamma carcinomas. By the combination of AG and AE on a receptor level in the tumor, not only is there an ovarian blockage as a result, but there is also blockage of the respective hormones evolving from other tissues. Therefore, a combination of AG and AE is suited for the therapy of premenopausal as well as postmenopausal mamma carcinoma. The combination of AG and AE and its use for the termination of pregnancy, induction of labor and for the treatment of gynecological disorders such as endometriosis and dysmenorrhea is discussed in co-pending application [Attorney Dock No. SCH 892] filed on even date.

The weight ratio of both components herein can be varied within wide limits for the treatment of the hormone-dependent tumors in a patient, e.g., mammals, including humans. Thus, equal amounts of AG and AE as well as an excess amount of one of the two components can be used. AG and AE are utilized jointly, separately, simultaneously and/or staggered in time (sequentially), in a weight ratio of about 1:50 to 50:1, preferably 1:30 to 30:1, and especially 1:15 to 15:1.

Preferably, AG and AE are administered combined in one dosage unit.

Suitable antigestagens include all compounds showing strong affinity to the gestagen receptor (progesterone receptor) while not displaying progestational activity on their own. Suitable competitive progesterone antagonists are, for example, but not limited to the following steroids:

11β-[(4-N,N-dimethylamino)phenyl]-17β-hydroxy-17α-propynyl-4,9(10)-estradien-3-one (RU-38486), 11β-[(4-N,N-dimethylamino)phenyl]-17β-hydroxy-18-methyl-17α-propynyl-4,9(10)-estradien-3-one;

11β-[(4-N,N-dimethylamino)phenyl]-17aβ-hydroxy-17aα-propynyl-D-homo-4,9(10),16-estratrien-3-one (all of them EP-A 0 057 115);

11β-p-methoxyphenyl-17β-hydroxy-17α-ethynyl-4,9(10)-estradien-3-one [Steroids 37: 361–382 (1981)] and 11β-(4-dimethylaminophenyl)-17α-hydroxy-17β-(3-hydroxypropyl)-13α-methyl-4,9-gonadien-3-one (EP-A 0 129 499).

Mixtures of the compounds can also be used.

The antigestagens can be utilized according to the present invention in amounts of 10 mg to 200 mg; generally, 50–100 mg of 11β-[4-N,N-dimethylamino)phenyl]-17α-hydroxy-17β-(3-hydroxypropyl)-13α-methyl-4,9(10)-gonadien-3-one per day, or a biologically equivalent amount of another antigestagen, will be sufficient.

Suitable compounds having anti-estrogenic activity are anti-estrogens and aromatase inhibitors, or mixtures thereof. Anti-estrogens and aromatase inhibitors according to the present invention can be derived from steroids or can also be nonsteroidal compounds. The anti-estrogens act as competitive estrogen antagonists in that they displace estrogen from the receptor whereas aromatase inhibitors suppress the biosynthesis of estrogen. Compounds such as the aminoglutethimides used in U.S. Pat. No. 4,670,426, i.e., 3-(4-aminophenyl)piperidine-2,6-diones alkylated in the 3-position and others which exert a lowering effect on other sexual hormone serum concentrations (e.g., progesterone) as well as in the estrogen level, are unsuitable according to this invention as compounds having anti-estrogen activity. Thus, compounds having anti-estrogenic activity in accordance with the present invention are to be understood to include those compounds having a maximally selective effect in this sense, i.e., excluding those which also inhibit the effect of sexual hormones other than estrogens, and/or lower their concentration.

Suitable anti-estrogens include conventional anti-estrogens meeting the above-recited conditions. They can be used approximately in the same quantities as the anti-estrogens already available commercially, i.e., the daily dosage is about 5-100 mg for tamoxifen or biologically equivalent amounts of another anti-estrogen. Suitable nonsteroidal anti-estrogens are, for example:

tamoxifen=(Z)-2-[p-(1,2-diphenyl-1-butenyl)phenoxy]-N,N-dimethylethylamine, nafoxidine=1-[2-[4-(6-methoxy-2-phenyl-3,4-dihydro-1-naphthyl)phenoxy]ethyl]pyrrolidine hydrochloride, Mer 25=1-[p-(2-diethylaminoethoxy)phenyl]-2-(p-methoxyphenyl)-1-phenylethanol, and compounds of the type of 1,1,2-triphenylbut-1-ene, especially 1,1-bis(3'-acetoxyphenyl)-2-phenybut-1-ene [J. Cancer Res. Clin. Oncol. 112: 119–124 (1986)].

Furthermore, suitable steroidal anti-estrogens include:

11α-methoxy-17α-ethynyl-1,3,5(10)-estratriene-3,17β-diol, and

16β-ethylestradiol, and 11-(3,17β-dihydroxy-1,3,5(10)-estratrien-7α-yl) undecanoic acid (N-butyl-N-methyl)amide (EP-A 0 138 504).

Mixtures can also be used.

Suitable aromatase inhibitors which can be used alone or in combination are all compounds inhibiting formation of estrogens from their precursors, such as, for example, 1-methylandrosta-1,4-diene-3,17-dione, described in German Laid-Open Application 3,322,285; testolactone (17a-oxa-D-homoandrosta-1,4-diene-3,17-dione) described in "Journal of Clinical Endocrinology and Metabolism" 49: 672 (1979); the compounds described in "Endocrinology" 1973, vol. 92, No. 3, page 874: androsta-4,6-diene-3,17-dione, androsta-4,6-dien-17β-ol-3-one acetate, androsta-1,4,6-triene-3,17-dione, 4-androstene-19-chloro-3,17-dione, 4-androstene-3,6,17-trione; the 19-alkynylated steroids disclosed in German Laid-Open Application 3,124,780; the 10-(1,2-propadienyl) steroids described in German Laid-Open Application 3,124,719; the 19-thioandrostane derivatives set forth in European Patent Application, Publication No. 100 566; 4-androsten-4-ol-3,17-dione, disclosed in "Endocrinology" 1977, vol. 100, No. 6, page 1684 and in U.S. Pat. No. 4,235,893, and its esters; the 1-methyl-15α-alkyl-androsta-1,4-diene-3,17-diones described in German Laid-Open Application 3,539,244; the 10β-alkynyl-4,9(11)-estradiene derivatives set forth in German Laid-Open Application 3,644,358; and 1,2β-methylene-6-methylene-4-androstene-3,17-dione disclosed in European Patent Application 0 250 262; or mixtures thereof.

An example of a nonsteroidal aromatase inhibitor is [4-(5,6,7,8-tetrahydroimidazo[1,5α]pyridin-5-yl) benzonitrile monohydrochloride] (Cancer Res. 48: 834–838, 1988).

The dosage can be about 1–1,000, preferably 1–600, mg per day of 1-methylandrosta-1,4-diene-3,17-dione, or biologically equivalent dosages of other aromatase inhibitors.

The compounds having antiprogestational and anti-estrogenic activities can, for example, be applied locally or topically, or administered subcutaneously, enterally or parenterally.

Especially suitable for enteral administration are tablets, dragees, capsules, pills, suspensions, or solutions; these can be conventionally prepared with the additives and excipients customary in galenic pharmacy. Suitable for local or topical application are, for example, vaginal suppositories or transdermal systems, such as skin plasters.

The subcutaneous injection, which is preferred, is carried out with an oily solution of the respective component(s).

An AG dosage unit can contain about 10–200 mg of 11β-[(4-N,N-dimethylamino)phenyl]-17α-hydroxy-17β-(3-hydroxypropyl)-13α-methyl-4,9(10)-gonadien-3-one; 10–200 mg of 11β-[(4-N,N-dimethylamino)phenyl]-17β-hydroxy-17β-(3-hydroxyprop-1(Z)-enyl)-4,9-estradien-3-one; or a biologically equivalent amount of another antigestagen.

An AE dosage unit can contain 1–100 mg of tamoxifen or 10–200 mg of 1-methylandrosta-1,4-diene-3,17-dione; 10–200 mg of 11-(3,17β-dihydroxy-1,3,5(10)-estratrien-7α-yl)undecanoic acid(N-butyl-N-methyl)amide; 10–200 mg of 1,1-bis(3'-acetoxyphenyl)-2-phenylbut-1-ene; or a biologically equivalent amount of another compound having anti-estrogenic activity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

BRIEF DESCRIPTION OF THE DRAWING

Various other objects, features and attendant advantages of the present invention will be more fully appreciated as the same becomes better understood when considered in conjunction with the accompanying drawing in which like reference characters designate the same or similar parts throughout the several views, and wherein:

FIG. 1 depicts the results of studies on hormone-dependent estrogen and progesterone-receptor-positive MXT(+) mamma carcinoma in mice.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application P 37 33 478.6 (the priority document), are hereby incorporated by reference.

EXAMPLE 1

10.0 mg 11β-[(4-N,N-Dimethylamino)phenyl]-17α-hydroxy-17β-(3-hydroxypropyl)-13α-methyl-4,9-gonadien-3-one 140.5 mg Lactose 69.5 mg Cornstarch 2.5 mg Polyvinylpyrrolidone 25

2.0 mg "Aerosil"

0.5 mg Magnesium stearate 225.0 mg Total weight of tablet

EXAMPLE 2

50.0 mg 1-Methylandrosta-1,4-diene-3,17-dione 115.0 mg Lactose 50.0 mg Cornstarch 2.5 mg Poly-N-vinylpyrrolidone 25

2.0 mg "Aerosil"

0.5 mg Magnesium stearate 220.0 mg Total weight of tablet

EXAMPLE 3

25.0 mg 1-Methylandrosta-1,4-diene-3,17-dione 25.0 mg 11β-[(4-N,N-Dimethylamino)phenyl]-17α-hydroxy-17β-(3-hydroxypropyl)-13α-methyl-4,9-gonadien-3-one 115.0 mg Lactose 50.0 mg Cornstarch 2.5 mg Poly-N-vinylpyrrolidone 25

2.0 mg "Aerosil"

0.5 mg Magnesium stearate 220.0 mg Total weight of tablet which is manufactured in the usual way on a tabletting press. If desired, the active ingredients according to this invention can also be pressed, with respectively one-half of the above-indicated additives, separately into a two-layer tablet.

EXAMPLE 4

10.0 mg Tamoxifen 10.0 mg 11β-[(4-N,N-Dimethylamino)phenyl]-17α-hydroxy-17β-(3-hydroxypropyl)-13α-methyl-4,9-gonadien-3-one 135.0 mg Lactose 60.0 mg Cornstarch 2.5 mg Poly-N-vinylpyrrolidone 25

2.0 mg "Aerosil"

0.5 mg Magnesium stearate 220.0 mg Total weight of tablet which is manufactured in the usual way on a tabletting press. If desired, the active ingredients according to this invention can also be pressed, with respectively one-half of the above-indicated additives, separately into a two-layer tablet.

The following Examples 5 through 12 relate to the compositions of oily solutions. The thus-prepared solutions are filled into ampoules.

EXAMPLE 5

100.0 mg Tamoxifen 343.4 mg Castor oil 608.6 mg Benzyl benzoate 1,052.0 mg=1 ml

EXAMPLE 6

55.0 mg 1-Methylandrosta-1,4-diene-3,17-dione 55.0 mg 11β-[(4-N,N-Dimethylamino)phenyl]-17α-hydroxy-17β-(3-hydroxypropyl)-13α-methyl-4,9-gonadien-3-one 343.4 mg Castor oil 608.6 mg Benzyl benzoate 1,062.0 mg=1 ml The active agents according to this invention can also be dispensed separately into two chambers with respectively one-half of the above-mentioned additives.

EXAMPLE 7

10 mg 11-(3,17β-Dihydroxy-1,3,5(10)-estratrien-7α-yl)-undecanoic acid (N-butyl-N-methyl)amide 0.9 ml Castor oil 0.1 ml Benzyl benzoate 1.0 ml

EXAMPLE 8

10 mg 11β-[(4-N,N-Dimethylamino)phenyl]-17α-hydroxy-17β-(3-hydroxypropyl)-13α-methyl-4,9-gonadien-3-one 0.9 ml Castor oil 0.1 ml Benzyl benzoate 1.0 ml

EXAMPLE 9

10 mg 1,1-Bis(3'-acetoxyphenyl)-2-phenylbut-1-ene 0.9 ml Olive oil 1.0 ml

EXAMPLE 10

10 mg 11β-[(4-N,N-Dimethylamino)phenyl]-17β-hydroxy-17α-(3-hydroxyprop-1(Z)-enyl)-4,9-estradien-3-one 0.9 ml Olive oil 1.0 ml

EXAMPLE 11

60 mg 11-(3,17β-Dihydroxy-1,3,5(10)-estratrien-7α-yl)-undecanoic acid (N-butyl-N-methyl)amide 10 mg 11β-[(4-N,N-Dimethylamino)phenyl]-17α-hydroxy-17β-(3-hydroxypropyl)-13α-methyl-4,9-gonadien-3-one 0.9 ml Castor oil 0.1 ml Benzyl benzoate 1.0 ml

EXAMPLE 12

60 mg 1,1-Bis(3'-acetoxyphenyl)-2-phenylbut-1-ene 10 mg 11β-[(4-N,N-Dimethylamino)phenyl]-17β-hydroxy-17α-(3-hydroxyprop-1(Z)-enyl)-4,9-estradien-3-one 1.0 ml Olive oil 1.0 ml

Results

The results of studies on hormone-dependent, estrogen- and progesterone-receptor-positive MXT(+) mamma carcinoma in mice (Watson, C., Medina, D., Clark, J. H., Cancer Res. 1977, 37: 3344–3348) can be seen from Tables 1 and 2, as well as from FIG. 1.

The MXT tumor used was the MXT line M 3.2 generously provided by Dr. A. E. Bogden, EG+G Bogden Laboratories, Worcester, Mass., USA as a frozen sample. After thawing, pieces (volume about 2 $mm^3$) were implanted subcutaneously into intact, female, 8–10 week old BDF1 mice (Charles River Wiga, F.R.G.). After the tumor had reached a diameter of about 1 cm, it was further passaged to BDF1 mice as will be described later. Tumors were taken from various transplant generations, frozen and kept in liquid nitrogen. To perform an experiment, tumor pieces from a frozen sample are implanted in 3–5 mice. In the next passage, the hormone dependency is tested by implantation in intact and ovariectomized mice (J. Med. Chem., 1985, 28: 1880–1885).

If there is inhibition of tumor growth in the ovariectomized mice of more than 90% after 6 weeks compared to the intact control, these tumors can be used for further testing. Two to three tumors from one to two donor animals are taken out, cut in pieces of about 2 mm in diameter in medium MEM 199 (MEM=Minimum Essential Medium). These pieces are implanted s.c. in BDF1 mice as above (2 tumors/mouse).

(a) Therapy of Established Tumors

Twenty days after tumor implantation, the mice are palpated for tumors. Only mice with two palpable tumors are used. These animals were randomly distributed in groups of 9–10. Treatment is started at the next day for 2 or 3 weeks. Test compounds are injected 6 times a week s.c. Tumor area was determined by caliper measurements once or twice weekly. Tumor area is the product of the longest diameter and its perpendicular diameter. At the end of treatment, the animals were killed and weighed. The tumors, ovaries, uteri, and vaginae were removed and the wet weights were determined (J. Med. Chem., loc. cit.).

(b) Prophylaxis Model

After tumor implantation, the animals are randomly distributed in groups of 9–10. On the next day, treatment is started. Test compounds are injected daily s.c. as oil solutions (10% benzyl benzoate) or ovariectomy is performed, respectively. After 6 weeks of treatment, the animals were processed as above.

(a) Therapy of Established Tumors

Compounds Having Anti-Estrogenic Activity

In the therapy of established tumors, a dose, administered six times weekly s.c., of 30 mg/kg of body weight of 11-(3,17β-dihydroxy-1,3,5(10)-estratrien-7α-yl)undecanoic acid (N-butyl-N-methyl)amide (=AE-A) resulted in a growth inhibition of 33% based on the tumor area.

Antigestagens

With the antigestagen 11β-[(4-N,N-dimethylamino)phenyl]-17α-hydroxy-17β-(3-hydroxypropyl)-13α-methyl-4,9-gonadien-3-one (=AG-B), a growth inhibition of 52% based on the tumor area was observed with s.c. administration of six times weekly 5 mg/kg of body weight.

AG/AE Combination

The combination of the two compounds AE-A and AG-B in the above-indicated doses brings about inhibition of 72% based on the tumor area. The effect of the combination is significantly higher (p<0.05) than the respective monotherapies, and even surpasses ovariectomy, though not significantly.

Using, for evaluating the tumor growth inhibition, the tumor weights rather than the tumor areas, comparable results are achieved, as can be seen from Table 1.

(b) Prophylactic Therapy of Tumors (Table 2)

In the prophylaxis model of the MXT(+) tumor wherein therapy is started immediately after implantation of the tumor and is continued for 6 weeks, the anti-estrogen 1,1-bis(3'-acetoxyphenyl)-2-phenylbut-1-ene (=AE-C) exhibits no significant antitumor activity (dose=8 mg/kg).

The antigestagen 11β-[(4-N,N-dimethylamino)phenyl]-17β-hydroxy-17α-(3-hydroxyprop-1(Z)-enyl)-4,9-estradien-3-one (=AG-D) inhibits tumor growth in this model, namely by 68%. The combination of the two aforementioned components AE-C and AG-D likewise leads to a marked enhancement of antitumor activity as compared with the antiprogestational component by itself.

TABLE 1

MXT(+) MAMMA CARCINOMA IN MICE
(THERAPY OF ESTABLISHED TUMORS)

|  | Tumor Area | | Tumor Weight | |
|---|---|---|---|---|
|  | (mm$^2$) | % T/C | (mg) | % T/C |
| Control | 251 ± 134 | 100 | 2199 ± 1185 | 100 |
| Ovariectomy | 113 ± 61 | 45 | 941 ± 368* | 43 |
| AE-A, 30 mg/kg | 168 ± 41 | 67 | 1579 ± 389 | 72 |
| AG-B, 5 mg/kg | 120 ± 62 | 48 | 976 ± 513* | 44 |
| AE-A, 30 mg/kg + AG-B, 5 mg/kg | 71 ± 23 | 28 | 487 ± 153* | 22 |

*p < 0.05 (U Test) versus Control
Dosage: 6 × weekly s.c. in castor oil/benzyl benzoate

TABLE 2

EFFECT OF AG-D ALONE AND IN COMBINATION WITH AE-C
USING THE MXT M 3.2 MAMMA TUMOR MODEL

| Compound | Dose (a) (mg/kg) | Tumor Weight (b) (% T/C) |
|---|---|---|
| 1. AG-D | 1.0 | 32* |
| AG-D + AE-C | 1.0 + 8.0 | 8* |
| 2. AG-D | 1.0 | 47* |
| AG-D + AE-C | 1.0 + 16.0 | 21* |

(a) Dose: 3 × weekly s.c. in olive oil
(b) Values after 6 weeks of therapy
% T/C Therapy Group/Control × 100
*p < 0.01 (U Test according to Wilcoxon)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising effective amounts of a compound having competitive progesterone antagonistic activity (AG) and a compound having anti-estrogenic (AE) activity, and a pharmaceutically acceptable carrier, wherein the AG and AE are present in a weight ratio of 1:50 to 50:1, and wherein the amounts of AG and AE are each ineffective or marginally effective, but when coadministered, have a synergistic effect in the treatment of a hormone-dependent tumor.

2. A pharmaceutical composition of claim 1, wherein the AG and AE are present in a weight ratio of 1:25 to 25:1.

3. A pharmaceutical composition of claim 2, wherein the AG and AE are present in a weight ratio of 1:10 to 10:1.

4. A pharmaceutical composition of claim 1, wherein the AG and AE are present in separate dosage units.

5. A pharmaceutical composition of claim 1, wherein the AG and AE are present in a combined unit dosage.

6. A pharmaceutical composition according to claim 1, wherein a compound having antiprogestational activity is 11β-[(4-N,N-dimethylamino)phenyl]-17β-hydroxy-17α-propynyl-4,9(10)-estradien-3-one; 11β-[(4,N,N-dimethylamino)phenyl]-17β-hydroxy-18-methyl-17α-propynyl-4,9(10)-estradien-3-one; 11β-[4,N,N-dimethylaminophenyl]-17aβ-hydroxy-17aα-propynyl-D-homo-4,9(10),16-estratrien-3-one; 11β-p-methoxyphenyl- 17β-hydroxy-17α-ethynyl-4,9(10)-estradien-3-one; 11β-(4-dimethylaminophenyl)-17α-hydroxy-17β-(3-hydroxypropyl)-13α-methyl-4,9,gonadien-3-one, or a mixture thereof.

7. A pharmaceutical composition of claim 1, wherein the compound having anti-estrogen activity is a competitive estrogen antagonist; an aromatase inhibitor, or a mixture thereof.

8. A pharmaceutical composition of claim 7, wherein the anti-estrogen is (Z)-2-[p-(1,2-diphenyl-1-butenyl)phenoxy]-N,N-dimethylethylamine;

1-[2-[4-(6-methoxy-2-phenyl-3,4-dihydro-1-naphthyl]phenoxy]ethyl]pyrrolidine hydrochloride;

1-[p-(2-diethylaminoethoxy)phenyl]-2-(p-methoxyphenyl)-1-phenylethanol;

11α-methoxy-17α-ethynyl-1,3,5(10)-estratriene-3,17β-diol; or

16β-ethylestradiol.

9. A pharmaceutical composition of claim 7, wherein the anti-estrogen is an aromatase inhibitor and is 1-methylandrosta-1,4-diene-3,17-dione;

testolactone (17a-oxa-D-homoandrosta-1,4-diene-3,17-dione);

androsta-4,6-diene-3,17-dione;

androsta-4,6-dien-17β-ol-3-one acetate;

androsta-1,4,6-triene-3,17-dione;

4-androstene-19-chloro-3,17-dione;

4-androstene-3,6,17-trione;

19-alkynylated steroids;

10-(1,2-propadienyl) steroids;

19-thioandrostane derivatives;

4-androsten-4-ol-3,17-dione, or one of its esters;

1,methyl-15α-alkyl-androsta-1,4-diene-3,17-dione;

10β-alkynyl-4,9(11)-estradiene derivatives;

1,2β-methylene-6-methylene-4-androstene-3,17-dione; or mixtures thereof.

10. A pharmaceutical composition of claim 1, wherein the amount of AG is 1–200 mg of 11β-[(4-N,N-dimethylamino)phenyl]-17α-hydroxy-17β-(3-hydroxypropyl)-13α-methyl-4,9(10)-gonadien-3-one, or a biologically equivalent amount of another compound having antiprogestational activity.

11. A pharmaceutical composition of claim 1, wherein the amount of AE is 1–100 mg of tamoxifen or a biologically equivalent amount of another compound having anti-estrogenic activity.

12. A pharmaceutical composition of claim 1, wherein the amount of AE is 10–200 mg of 1-methylandrosta-1,4-diene-3,7-dione or a biologically equivalent amount of another compound having anti-estrogenic activity.

13. A pharmaceutical composition of claim 9, wherein the amount of AE is 10–200 mg of 1-methylandrosta-1,4-diene-3,17-dione or a biologically equivalent amount of another compound having anti-estrogenic activity.

14. A pharmaceutical composition of claim 10, wherein the amount of AE is 10–200 mg of 1-methylandrosta-1,4-diene-3,17-dione or a biologically equivalent amount of another compound having anti-estrogenic activity.

15. A pharmaceutical composition of claim 9, wherein the AE and AG are in the same dosage unit.

16. A pharmaceutical composition of claim 1, wherein the AE is a 3,17-dihydroxy-7α-yl-1,3,5(10)-estratriene.

17. A pharmaceutical composition of claim 1, wherein the AG is a steroid.

18. A pharmaceutical composition of claim 16, wherein the AG is a steroid.

19. A pharmaceutical composition of claim 18, wherein the AG is a 4,9-estradien-3-one, a 4,9,16-estratrien-3-one or 4,9-gonadien-3-one.

20. A pharmaceutical composition of claim 16, wherein the AG is a 4,9-estradien-3-one, a 4,9,16-estratrien-3-one or a 4,9-gonadien-3-one.

21. A pharmaceutical composition of claim 20, wherein the AG is 11β-[(4-N,N-dimethylamino)phenyl]-17α-hydroxy-17β-(3-hydroxypropyl)-13α-methyl-4,9-gonadien-3-one and the AE is 11-(3,17β-dihydroxy-1,3,5(10)-estratrien-7α-yl)undecanoic acid-(N-butyl-N-methyl)amide.

22. A method for the treatment of a hormone-dependent tumor, comprising administering to a patient in need of such treatment effective amounts of a compound having competitive progesterone antagonistic activity (AG) and a compound having anti-estrogenic (AE) activity, wherein the AG and AE are administered in a weight ratio of 1:50 to 50:1, and wherein the amounts of AG and AE are each ineffective or marginally effective, but when coadministered, have a synergistic effect in the treatment of a hormone-dependent tumor.

23. A method of claim 22, wherein the AG and AE are administered in a weight ratio of 1:30 to 30:1.

24. A method of claim 23, wherein the AG and AE are administered in a weight ratio of 1:15 to 15:1.

25. A method of claim 22, wherein the AG and AE are administered in separate dosage units.

26. A method of claim 22, wherein the AG and AE are administered in a combined unit dosage.

27. A method according to claim 22, wherein the at least one compound having antiprogestational activity is 11β-[(4-N,N-dimethylamino)phenyl]-17β-hydroxy-17α-propynyl-4,9(10)-estradien-3-one;

11β-[(4,N,N-dimethylamino)phenyl]-17β-hydroxy-18-methyl-17α-propynyl-4,9(10)-estradien-3-one;

11β-[4,N,N-dimethylaminophenyl]-17aβ-hydroxy-17aα-propynyl-D-homo-4,9(10),16-estratrien-3-one;

11β-p-methoxyphenyl-17β-hydroxy-17α-ethynyl-4,9(10)-estradien-3-one;

11β-(4-dimethylaminophenyl)-17α-hydroxy-17β-(3-hydroxypropyl)-13α-methyl-4,9,gonadien-3-one, or a mixture thereof.

28. A method of claim 22, wherein the compound having anti-estrogen activity is a competitive estrogen antagonist, an aromatase inhibitor, or a mixture thereof.

29. A method of claim 22, wherein the anti-estrogen is (Z)-2-[p-(1,2-diphenyl-1-butenyl)phenoxy]-N,N-dimethylethylamine;

1-[2-[4-(6-methoxy-2-phenyl-3,4-dihydro-1-naphthyl]phenoxy]ethyl]pyrrolidine hydrochloride;

1-[p-(2-diethylaminoethoxy)phenyl]-2-(p-methoxyphenyl)-1-phenylethanol;

1,1-bis(3'-acetoxyphenyl)-2-phenylbut-1-ene;

11α-methoxy-17α-ethynyl-1,3,5(10)-estratriene-3,17β-diol;

11-(3,17β-dihydroxy-1,3,5(10)-estratrien-7α-yl)undecanoic acid(N-butyl-N-methyl)amide; or 16β-ethylestradiol.

30. A method of claim 28, wherein the aromatase inhibitor is 1-methylandrosta-1,4-diene-3,17-dione;

testolactone (17a-oxa-D-homoandrosta-1,4-diene-3,17-dione);

androsta-4,6-diene-3,17-dione;
androsta-4,6-dien-17β-ol-3-one acetate;
androsta-1,4,6-triene-3,17-dione;
4-androstene-19-chloro-3,17-dione;
4-androstene-3,6,17-trione;
19-alkynylated steroids;
10-(1,2-propadienyl) steroids;
derivatives of 19-thioandrostane;
4-androsten-4-ol-3,17-dione, or one of its esters;
1-methyl-15α-alkyl-androsta-1,4-diene-3,17-dione;
10β-alkynyl-4,9(11)-estradiene derivatives;
1,2β-methylene-6-methylene-4-androstene-3,17-dione;
[4-(5,6,7,8-tetrahydroimidazo[1,5α]pyridin-5yl)-benzonitrile monohydrochloride;
or mixtures thereof.

31. A method of claim 22, wherein the amount of AG is 10–200 mg of 11β-[(4-N,N-dimethylamino)phenyl]-17α-hydroxy-17β-(3-hydroxypropyl)-13α-methyl-4,9(10)-gonadien-3-one, or a biologically equivalent amount of another compound having antiprogestational activity.

32. A method of claim 22, wherein the amount of AE is 1–100 mg of tamoxifen or a biologically equivalent amount of another compound having anti-estrogenic activity.

33. A method of claim 22, wherein the amount of AE is 10–200 mg of 1-methylandrosta-1,4-diene-3,17-dione or a biologically equivalent amount of another compound having anti-estrogenic activity.

34. A method of claim 22, wherein the amount of AG is 10–200 mg of 11β-[4-N,N-dimethylamino)phenyl]-17β-hydroxy-17α-(3-hydroxyprop-1(Z)-enyl)-4,9-estradien-3-one.

35. A method according to claim 22, wherein the amount of AE is 10–200 mg of 11-(3,17β-dihydroxy-1,3,5(10)-estratrien-7α-yl)undecanoic acid(N-butyl-N-methyl)amide.

36. A method according to claim 22, wherein the amount of AE is 10–200 mg of 1,1-bis(3'-acetoxyphenyl)-2-phenylbut-1-ene.

37. A method of claim 22, wherein the AG and AE are administered sequentially.

38. A method of claim 37, wherein the sequence of administration is first, administration of one compound alone, followed by coadministration of both compounds.

39. A method of claim 37, wherein the sequence of administration is first, administration of one compound alone, followed by administration of the other compound alone.

40. A method of claim 37, wherein the AG is administered first.

41. A method of claim 37, wherein the AE is administered first.

42. A method of claim 22, wherein the AE is a 3,17-dihydroxy-7α-yl-1,3,5(10)-estratriene.

43. A method of claim 22, wherein the AG is a steroid.

44. A method of claim 42, wherein the AG is a steroid.

45. A method of claim 44, wherein the AG is a 4,9-estradien-3-one or 4,9-gonadien-3-one.

46. A method of claim 42, wherein the AG is a 4,9-estradien-3-one, a 4,9,16-estratrien-3-one or a 4,9-gonadien-3-one.

47. A method of claim 46, wherein the AG is 11β-[(4-N,N-dimethylamino)-phenyl]- 17α-hydroxy-17β-(3-hydroxypropyl)-13α-methyl-4,9-gonadien-3-one and the AE is 11-(3,17β-dihydroxy-1,3,5(10)-estratrien-7α-yl)undecanoic acid-(N-butyl-N-methyl)amide.

* * * * *